US006806017B2

(12) United States Patent
Reeves et al.

(10) Patent No.: US 6,806,017 B2
(45) Date of Patent: Oct. 19, 2004

(54) ELECTROSTATIC APPLICATION OF POWDER MATERIAL TO SOLID DOSAGE FORMS

(75) Inventors: Linda Ann Reeves, Chislehurst (GB); David Hoover Feather, San Diego, CA (US); Douglas Howard Nelson, Carlsbad, CA (US); Marshall Whiteman, Ditton (GB)

(73) Assignee: Phoqus Limited, West Malling (GB)

( * ) Notice: Subject to any disclaimer, the term of this patent is extended or adjusted under 35 U.S.C. 154(b) by 0 days.

(21) Appl. No.: 10/149,898

(22) PCT Filed: Dec. 15, 2000

(86) PCT No.: PCT/US00/33962

§ 371 (c)(1),
(2), (4) Date: Dec. 19, 2002

(87) PCT Pub. No.: WO01/43727

PCT Pub. Date: Jun. 21, 2001

(65) Prior Publication Data

US 2003/0211229 A1 Nov. 13, 2003

(30) Foreign Application Priority Data

Dec. 17, 1999 (GB) .............................. 9929946

(51) Int. Cl.[7] .............................. G03G 13/20; A61J 3/07
(52) U.S. Cl. ...................... 430/126; 430/124; 427/2.14; 427/458; 118/620
(58) Field of Search .................. 430/126, 124, 430/9; 427/2.14, 458, 2.1, 475; 118/620, 300

(56) References Cited

U.S. PATENT DOCUMENTS

| | | | |
|---|---|---|---|
| 3,536,034 A | | 10/1970 | Lecrone |
| 3,961,849 A | | 6/1976 | Jones |
| 4,106,868 A | | 8/1978 | Ophey |
| 4,912,003 A | | 3/1990 | Asanae et al. |
| 4,925,670 A | | 5/1990 | Schmidt |
| 5,006,362 A | | 4/1991 | Hilborn |
| 5,656,080 A | * | 8/1997 | Staniforth et al. ............ 118/20 |
| 6,117,479 A | * | 9/2000 | Hogan et al. .............. 427/2.14 |
| 6,406,738 B1 | * | 6/2002 | Hogan et al. .............. 427/2.14 |
| 2002/0197388 A1 | * | 12/2002 | Brown et al. ................ 427/2.1 |

FOREIGN PATENT DOCUMENTS

| | | |
|---|---|---|
| GB | 1 449 993 | 9/1976 |
| GB | 2 253 164 A | 9/1992 |
| JP | 59125766 A | 7/1984 |
| WO | 92/14451 | 9/1992 |
| WO | 96/35413 | 11/1996 |
| WO | 96/35516 | 11/1996 |

* cited by examiner

*Primary Examiner*—John L Goodrow
(74) *Attorney, Agent, or Firm*—Burns, Doane, Swecker & Mathis, L.L.P.

(57) ABSTRACT

In a method of electrostatically applying a powder material to a solid dosage form, charged powder material is applied to a photoconductive drum (3), is transferred to an intermediate belt (4) and then to a solid dosage form (5). The belt (4) makes contact with the solid dosage form (5).

32 Claims, 2 Drawing Sheets

ELECTROSTATIC APPLICATION OF POWDER MATERIAL TO SOLID DOSAGE FORMS

The present invention relates to a method and apparatus for the electrostatic application of powder material onto the surfaces of solid dosage forms, and more particularly, but not exclusively, pharmaceutical solid dosage forms.

A "solid dosage form" can be formed from any solid material that can be apportioned into individual units; it may be, but is not necessarily, an oral dosage form. Examples of pharmaceutical solid dosage forms include pharmaceutical tablets, pharmaceutical pessaries, pharmaceutical bougies and pharmaceutical suppositories. The term "pharmaceutical tablet" should be interpreted as covering all pharmaceutical products which are to be taken orally, including pressed tablets, pellets, capsules and spherules. Examples of non-pharmaceutical solid dosage forms include items of confectionery and washing detergent tablets.

The electrostatic application of powder material to solid dosage forms is known. In the known techniques, the powder is generally applied directly onto the solid dosage forms, either by spraying electrostatically charged powder material onto the solid dosage forms, or by holding the powder material at a potential difference to the solid dosage forms sufficient to cause the powder material to be attracted to the solid dosage forms. For example, WO92/14451 describes a process in which the cores of pharmaceutical tablets are conveyed on an earthed conveyor belt and electrostatically charged powder material is sprayed onto the tablet cores to form a powder coating on the exposed surface of the tablet cores. WO96/35516 describes a process in which the cores of pharmaceutical tablets are held substantially isolated from their surroundings adjacent to a source of powder at a potential difference to the tablet cores sufficient to cause the exposed surface of the tablet cores to become coated with the powder.

The present invention provides a method of electrostatically applying a powder material to a solid dosage form, the method comprising the steps of electrostatically applying a powder material to a first intermediate means, and transferring the powder material that has been applied to the first intermediate means from the first intermediate means to the solid dosage form.

Applying the powder material to a first intermediate means before it is applied to the solid dosage form has certain advantages. It becomes possible to provide an arrangement in which the location of the deposition of the powder material can be closely controlled and, for example, enables powder material to be deposited on a solid dosage form in a precise pattern. It may also facilitate the deposition of powder material on a three dimensional surface.

Any suitable method may be used to apply the powder material electrostatically to the first intermediate means. For example, the first intermediate means may be earthed and the powder material held at a potential sufficient to cause the powder material to adhere to the first intermediate means.

In a preferred embodiment of the invention the powder material is applied to the first intermediate means by applying an electrostatic charge to the first intermediate means, and holding the powder material at a potential sufficiently different from the potential of the first intermediate means to cause the powder material to adhere to the first intermediate means.

A first especially advantageous feature of a preferred embodiment of the invention is that the electrostatic charge may be applied to the first intermediate means in a pattern, making it possible to apply powder material onto a solid dosage form in the form of a pattern. Any desired pattern may be produced simply by applying a suitable electrostatic charge pattern to the first intermediate means. Thus, it is, for example, possible to print onto a solid dosage form the name or the dosage of the solid dosage form, or to apply to the solid dosage form a logo or some other design. By using different coloured powder materials, it is also possible to produce a pattern but at the same time have an uninterrupted coating on the solid dosage form. For example, different coloured powder materials could be used to produce a solid dosage form having a striped coating over all of the surface of a region of the solid dosage form or over the whole of the solid dosage form.

Where a coating is applied to parts only of a region being coated, the coating is referred to herein as discontinuous, even though in the case of, for example, joined up writing each part of the coating may be continuous with the other parts.

The electrostatic charge does not have to be applied to the first intermediate means in a pattern. It may be applied to the first intermediate means over the whole of a surface portion thereof. Accordingly, a conventional unpatterned and uninterrupted coating may be formed, if desired. Such a coating is referred to herein as a continuous coating but it will be understood that it may or may not, for example, cover all of a surface of a solid dosage form.

In the case where an electrostatic charge is applied to the first intermediate means, that means may be any means which is capable of maintaining an electrostatic charge on its surface. For example, the first intermediate means may be in the form of a drum or a belt and may comprise a photoconductive semi-conductor at its surface. A photoconductive semi-conductor is a material which conducts electricity on exposure to light, but behaves as an insulator in the absence of light. An electrostatic charge pattern may be applied to such a first intermediate means by electrostatically charging the semi-conductor in the dark, and then projecting an image onto the semi-conductor. The electrostatic charge will be dissipated in the illuminated areas, but will be retained in the unilluminated areas. Thus, an electrostatic charge pattern in the shape of the image will be formed on the semi-conductor. Such first intermediate means are used in conventional photocopiers as photoconductive drums or belts. For example, a photoconductive drum used in the present invention may be a conductive drum coated with selenium, selenium/arsenic or selenium/tellurium, or a conductive drum coated with a thin layer of photoconductive pigment in a binder resin, and a charge transport layer coated over the photoconductive pigment layer. A photoconductive belt used for the invention may be a flexible conductive substrate coated with photogenerator layer comprising a photoconductive pigment in a binder polymer overcoated with a charge transport layer.

The powder material should possess a defined electrostatic charge which is either (a) of the same sign of charge as the residual charged area pattern on the photoconductive drum or belt after light exposure, or (b) of opposite sign of charge to the residual charged pattern on the photoconductive drum or belt after light exposure. In the case (a) the powder will be developed onto the areas of the photoconductive drum, or belt, which have been discharged, i.e. the light illuminated areas, and will be repelled by the areas of the photoconductive drum, or belt, which remain charged. Conversely in case (b) the powder will be developed onto the areas of the photoconductive drum, or belt, which remain charged, and will not be developed onto areas of the photoconductive drum, or belt, which have been discharged, i.e. the light illuminated areas. The powder material may have a permanent or temporary net charge. Any suitable method may be used to charge the powder material. Advantageously, the electrostatic charge on the powder material is imparted by a triboelectric charging process (as is common in conventional photocopying) or by corona charging.

Any suitable method may be used to apply the charged powder onto the first intermediate means. Methods have already been developed in the fields of electrophotography and electrography and examples of suitable methods are described, for example, in Electrophotography and Development Physics, Revised Second Edition, by L. B. Schein, published by Laplacian Press, Morgan Hill Calif.

A second especially advantageous feature of a preferred embodiment of the invention is that there is contact between the first intermediate means and the solid dosage form during transfer of the powder material from the intermediate to the solid dosage form. Contact between the first intermediate means and the solid dosage form increases the accuracy and speed and completeness with which the powder can be transferred to the dosage form. That may be advantageous irrespective of the method used to apply the powder material electrostatically to the first intermediate means. However, it is particularly advantageous where the powder material is applied in the form of a pattern.

The solid dosage form will, in general, be a three-dimensional object. For example, a conventionally-shaped pharmaceutical tablet comprises an upper domed surface and a lower domed surface, the two domed surfaces being joined together by an edge surface. In the known techniques where powder material is applied directly onto the solid dosage form, it is difficult to obtain uniform application of powder material, especially to the edges of the solid dosage form.

Accordingly, preferably, the first intermediate means conforms partially or completely to the shape of the solid dosage form on transfer of the powder material to the solid dosage form. In the case where the solid dosage form is a pressed tablet of domed shape the first intermediate means may conform only to the shape of the domed part of the tablet or may also contact the cylindrical side wall of the tablet.

If the first intermediate means is able to conform to the shape of the solid dosage form, it becomes possible to transfer powder material with greater uniformity to the edges of the solid dosage form. That may be advantageous irrespective of the method used to apply the powder material to the first intermediate means. Where the powder material has been applied to the first intermediate means in a discontinuous manner to form a pattern, it also becomes possible to reduce or even eliminate distortion of the pattern on transfer of the powder to the edges of the solid dosage form.

Any suitable method may be used to transfer powder material from the first intermediate means to the solid dosage form. The powder material that adheres to the first intermediate means may be transferred from the first intermediate means to the solid dosage form, at least partly, by electrostatic means. For example, the solid dosage form may be held at a potential sufficient to overcome the attractive forces of the powder material to the first intermediate means, and to cause the powder material to adhere to the solid dosage form instead. Alternatively, or in addition, the powder material that adheres to the first intermediate means may be transferred from the first intermediate means to the solid dosage form at least partly by heating the powder material during the transfer, and/or at least partly by means of pressurised contact between the first intermediate means and the solid dosage form.

If there is only one intermediate means, it must be possible to apply powder material electrostatically to that intermediate means, and to substantially transfer the powder material from that intermediate means to the solid dosage form. However, the properties required for the electrostatic application are not always compatible with the properties required for the transfer to the solid dosage form, particularly if the first intermediate means also has to be especially flexible.

Accordingly, a third especially advantageous feature of a preferred embodiment of the invention is that the powder material that has been applied to the first intermediate means is transferred from the first intermediate means to the solid dosage form via a second intermediate means. The first intermediate means then requires only those properties which are necessary for electrostatic application of the powder material to the first intermediate means, and the second intermediate means requires only those properties which are necessary to enable powder material to be transferred from the first intermediate means to the second intermediate means and from the second intermediate means to the solid dosage form.

Advantageously, there is contact between the first intermediate means and the second intermediate means on transfer of the powder material from the first intermediate means to the second intermediate means. Advantageously, there is contact between the second intermediate means and the solid dosage form on transfer of the powder material from the second intermediate means to the solid dosage form. More advantageously, the second intermediate means conforms partially or completely to the shape of the solid dosage form on transfer of the powder material to the solid dosage form. The second intermediate means may be in the form of a drum or a belt and may comprise an elastomeric material, for example a silicone rubber, that may be sufficiently soft to deform as required. Elastomeric materials used for the construction of the second intermediate means are, for example, rubber materials of defined durometer hardness. Durometer hardness can be described by the Shore A hardness scale. Materials particularly suitable would be, for example, silicone rubber with durometer hardness in the range 10A to 90A on the Shore A scale.

Electrostatic forces may also cause or contribute to the transfer of the powder material from the first intermediate means to the second intermediate means and/or from the second intermediate means to the solid dosage form.

Preferably, the method further comprises the step of treating the powder material to fix it on the solid dosage form. Where the powder material has been applied in a continuous manner, the treatment may result in the formation of a continuous coating on the solid dosage form.

The treatment of the powder material to secure it to the solid dosage form preferably involves a heating step, preferably using convection, but other forms of heating such as infra red radiation or conduction or induction may be used. The powder material should be heated to a temperature above its softening point, and then allowed to cool to a temperature below its glass transition temperature (Tg). Where the powder material has been applied in a discontinuous manner, it may be desirable to ensure that too much heat is not applied as the powder material may spread once it has fused, and that may result in distortion or even loss of the pattern. It is also important to control the amount of heat applied to avoid degradation of the powder material and/or the solid dosage form. The amount of heat required may be reduced by applying pressure to the powder material during the transfer step. Alternatively, the powder material may include a polymer which is cured during the treatment, for example, by irradiation with energy in the gamma, ultra violet or radio frequency bands.

The powder material may be treated to fix it on the solid dosage form as it is being transferred to the solid dosage form. For example, where there is contact between the solid dosage form and the first intermediate means or the second intermediate means on transfer of the powder material to the solid dosage form, fusing may be achieved by using the first intermediate means or the second intermediate means to apply heat with or without pressure to the solid dosage form. Alternatively, the treatment may be carried out after the powder material has been transferred to the solid dosage form.

The method may comprise the step of applying powder material to a first surface of the solid dosage form, and the subsequent step of applying powder material to a second surface of the solid dosage form. Such a step will usually be necessary if the whole surface of the dosage form is to be coated.

Preferably, the method is carried out as a continuous process.

The method of the present invention is not restricted to the use of any particular type of powder material. The powder materials described in PCT/GB96/01101 are examples of suitable powder materials.

The powder material may include an active material, for example a biologically active material, that is, a material which increases or decreases the rate of a process in a biological environment. The biologically active material may be one which is physiologically active.

Conventionally, where an active material is to be administered in solid dosage form, the active material is mixed with a large volume of non-active "filler" material in order to produce a dosage form of manageable size. It has been found, however, that it is difficult to control accurately the amount of active material contained in each dosage form, leading to poor dose uniformity. That is especially the case where the required amount of active material in each dosage form is very low.

By electrostatically applying active material to a dosage form, it has been found to be possible to apply accurately, and reproducibly, very small amounts of active material to the dosage form, leading to improved dose reproducibility.

The powder material comprising active material may be applied to a solid dosage form containing the same or a different active material, or may be applied to a solid dosage form containing no active material.

The present invention further provides an apparatus for electrostatically applying a powder material to a solid dosage form, the apparatus comprising means for applying a powder material to a first intermediate means, and means for transferring the powder material that has been applied to the first intermediate means from the first intermediate means to the solid dosage form, or a means for transferring the powder material that has been applied to the first intermediate means from the first intermediate means to a second intermediate means and means for transferring the powder material subsequently from the second intermediate means to the solid dosage form.

The apparatus of the invention may be in a form suitable for carrying out the method of the invention in any of the forms described above.

By way of example, methods of electrostatically applying powder material onto the surface of a pharmaceutical solid dosage form will now be described with reference to the accompanying drawings in which FIG. 1 shows schematically a first form of apparatus according to the invention;

Figure 1:
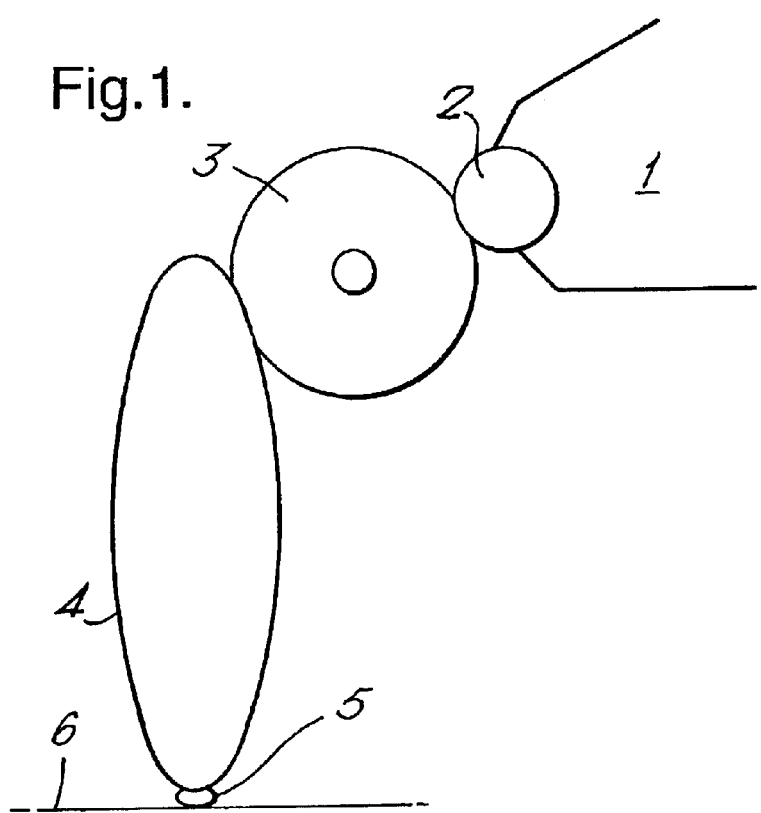

The apparatus shown schematically in FIG. 1 is for printing powder material onto a single surface of a pharmaceutical pressed tablet. The apparatus comprises a reservoir 1 for charged powder material. Downstream of the reservoir 1 is a rotatable developer roller 2 for transferring charged powder material from the reservoir 1 to a first intermediate means comprising a rotatable imaging drum 3 to which an electrostatic charge pattern of opposite charge to the charge of the powder material has been applied. The imaging drum 3 is a selenium-coated drum similar to those used in conventional photocopiers. Downstream of the imaging drum 3 is a second intermediate means comprising a rotatable intermediate belt 4 for transferring the powder material that adheres to the imaging drum 3 to a pharmaceutical tablet 5 carried on a conveyor belt 6. The intermediate belt 4 is able to conform to the cylindrical shape of the imaging drum 3 and also to the domed shape of the pharmaceutical tablet 5.

In use, an electrostatic charge is applied to the powder material as it leaves the reservoir 1. The developer roller 2 rotates, and as it rotates a layer of charged powder material is applied to its outer surface from the reservoir 1. An electrostatic charge of opposite charge to the charge on the powder material is applied to the imaging drum 3 by electrostatically charging the drum 3 in the dark. An image is then projected onto the drum 3 and the electrostatic charge dissipates in the illuminated areas, but is retained in the non-illuminated areas. Because the powder material is to be transferred from the imaging drum 3 to the pharmaceutical tablet 5 via the intermediate belt 4, the latent electrostatic image should be a true image of the desired final pattern. The rotating developer roller 2 applies the charged powder material to the imaging drum 3, which also rotates. The charged powder material adheres to those parts of the imaging drum 3 to which an electrostatic charge pattern has been applied, and retained. The intermediate belt 4 rotates, and as it rotates it conforms to the shape of the imaging drum 3 and the pharmaceutical tablet 5. In order to conform to the shape of the tablet 5, the belt 4 has to be able to curve about two orthogonal horizontal axes. Powder material on the imaging drum 3 is transferred to the intermediate belt 4 and then to the pharmaceutical tablet 5. Transfer from the imaging drum 3 to the intermediate belt 4 and from the intermediate belt 4 to the pharmaceutical tablet 5 can be promoted by applying suitable electrical potentials to the belt 4 and the pharmaceutical tablet 5 at least in the region of each transfer. The powder material that has been applied to the pharmaceutical tablet 5 will be in the pattern corresponding to the non-illuminated pattern on the imaging drum 3 The conveyor belt 6 then carries the pharmaceutical tablet 5 to a fusing station (not shown) where the powder material that has been applied to the tablet 5 is fused and becomes fixed on the tablet 5.

While one particular embodiment of the invention has been described with reference to the drawings, it will be understood that many modifications may be made to the arrangement. For example, the imaging drum 3 may be held at earth potential; in such a case the belt 4 and the roller 2 may both be held at, say, positive potentials. Also the intermediate belt 4 may be in the form of a rotatable roller rather than a belt, and/or some other form of conveying means, apart from a conveyor belt, may be employed.

As will be understood from the description above, it is also possible for the intermediate belt 4 to be omitted altogether, so that powder passes from the imaging drum 3 directly to the tablets 5. Again, various different charging arrangements may be employed, including one in which the imaging drum 3 is held at earth potential and the development roll charged to, say, a positive potential.

Figure 2:
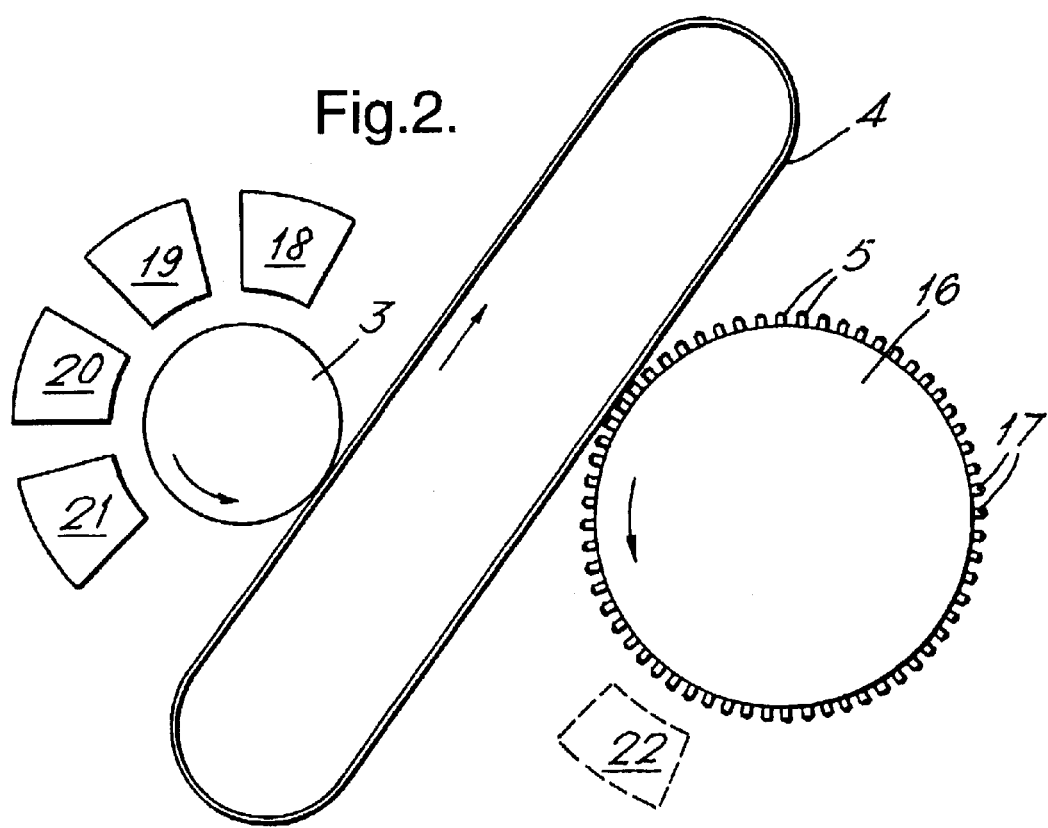
FIG. 2 is a diagrammatic view of the form of apparatus shown in FIG. 1 and illustrating further features of the apparatus.
Figure 2A:
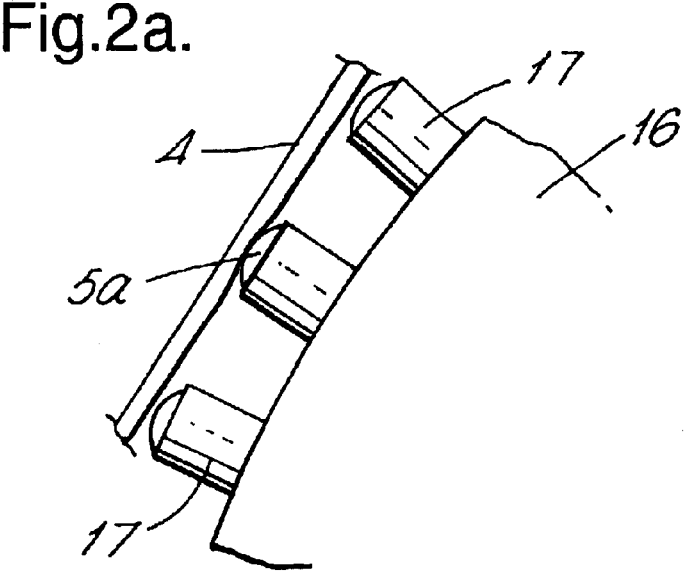
FIG. 2a is a view to a larger scale showing a detail of the apparatus of FIG. 2.

FIG. 2 illustrates some additional features of the same kind of apparatus as that schematically illustrated in FIG. 1 and corresponding parts are referenced by the same reference numerals. Whereas in FIG. 1 the tablets 5 are shown as being conveyed on a conveyor belt 6, in FIG. 2 the tablets 5 are shown on the periphery of a tablet drum 16 which has a plurality of tablet holders 17 around its periphery. The tablets 5 are retained on the tablet drum 16 by the application of reduced pressure to the inner faces of the tablet, for example as described in WO96/35516, the description of which is incorporated herein by reference. As can be seen in FIG. 2a, the intermediate belt 4 is sufficiently flexible that when brought into contact with the outer domed faces 5a of the tablets 5 it deforms, with the result that much of each domed face makes contact with the belt 4.

FIG. 2 also shows the various stations around the imaging drum 3, by which powder is applied to the drum in a predetermined pattern. The drum 3 is arranged to rotate anticlockwise as seen in FIG. 2 and the stations that the drum passes as it rotates anticlockwise as seen in FIG. 2 are a cleaning station 18, a charging station 19, an exposing station 20 and a developing station 21. Each of the stations may be of a kind well known per se in the field of electrophotography and their construction will not be described in detail here.

In use, a region of the drum 3 that has just ceased contact with the intermediate belt 4 passes first to the cleaning station 18 where any powder material still remaining on the drum is removed. That region of the drum 3 next passes to the charging station 19 where a uniform electrostatic charge (opposite to the charge of the powder material to be applied) is applied to the drum. Then, that region of the drum passes to the exposing station 20 where a pattern of light is projected onto the drum, discharging the electrostatic charge from selected regions of the drum and leaving a pattern of charge on the drum, that charge pattern corresponding to the pattern in which the powder material is to be applied to the tablets 5. Finally, at the developing station 21, charged powder material is applied, for example by the developer roller 2, to the drum 3 and adheres to the portions of the drum on which the electrostatic charge has been retained.

The patterned deposit of powder on the drum 3 travels round into contact with the belt 4 and is transferred to the belt 4 with which it makes rolling contact. The pattern is then carried on the belt 4 (which travels in a clockwise direction as seen in FIG. 2) and into contact with tablets 5 on the drum 16 as already described with reference to FIGS. 2 and 2a. After a tablet 5 has been carried into contact with the belt 4 on the drum 16 it is carried away by the drum in a clockwise direction as seen in FIG. 2 and may be carried past a fusing station 22, shown in dotted outline, where the powder material is fused and becomes fixed on the tablet 5.

If desired, the process described above with reference to FIGS. 2 and 2a can be repeated in order to coat the opposite domed faces of the tablets 5.

Figure 3:
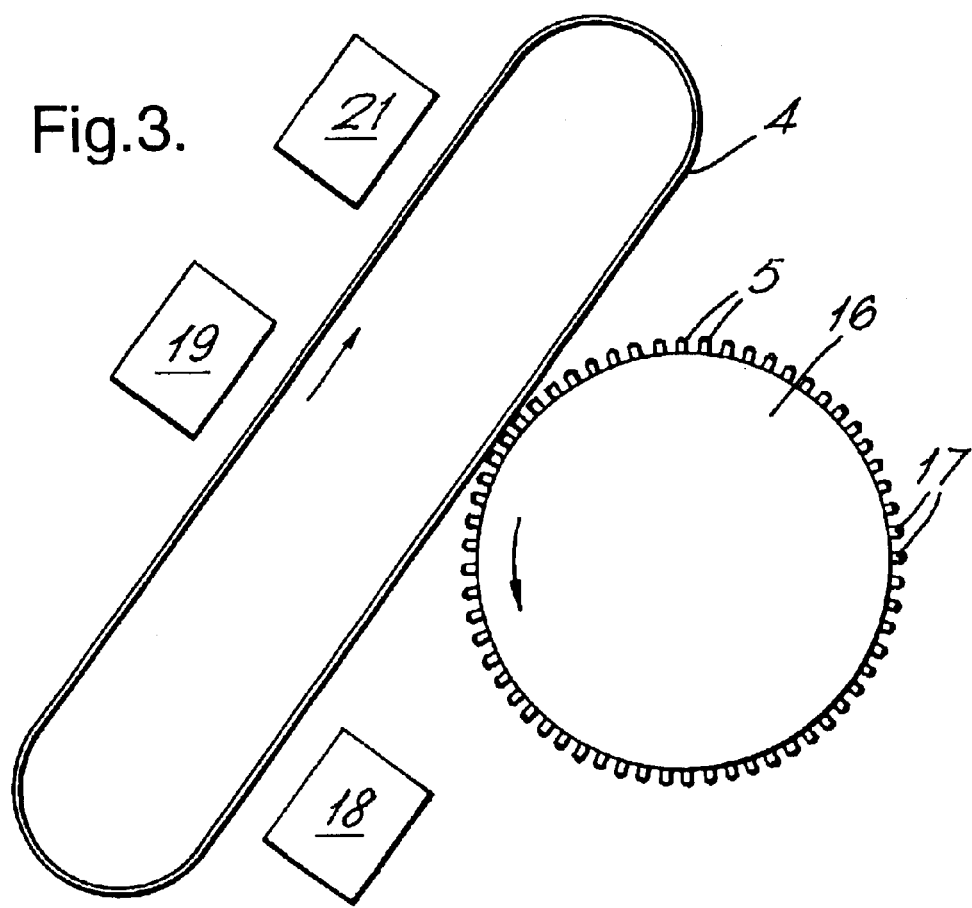
FIG. 3 is a diagrammatic view similar to FIG. 2 but showing a modified form of the apparatus of FIG. 2.

FIG. 3 illustrates a modified form of the apparatus of FIG. 2 and corresponding parts are referenced by the same reference numerals. The apparatus of FIG. 3 performs the same functions as that of FIG. 2 but most of the functions of the imaging drum 3 of FIG. 2 are performed by the belt 4 of FIG. 2 and the imaging drum 3 is omitted. In the apparatus of FIG. 3, a cleaning station 18, a charging station 19 and a developing station 21 are provided around the belt 4, but no exposing station is present. Thus the belt 4 is uniformly charged over its entire exposed face when it arrives at the developing station 21 and powder material is therefore deposited uniformly over the belt 4; the belt 4 rotates clockwise and the tablet drum 16 rotates anticlockwise as seen in FIG. 3 and powder material is transferred from the belt onto the domed faces of the tablets 5 as they come into contact with the belt 4. In this case, however, the powder coating is not patterned. As will be understood, the belt 4 of FIG. 3 need not exhibit photo-conductive properties. An alternative arrangement, however, would be to employ a photo-conductive belt as the belt 4 in FIG. 3 and furthermore to provide an exposing station between the charging station 19 and the developing station 21; in that case a patterned layer of powder material could be applied to the tablets 5.

If desired, the process described above with reference to FIG. 3 can be repeated in order to coat the opposite domed faces of the tablets 5.

What is claimed is:

1. A method of electrostatically applying a powder material to a solid dosage form, the method comprising the steps of electrostatically applying a powder material to a first intermediate means, and transferring the powder material that has been applied to the first intermediate means from the first intermediate means to the solid dosage form, wherein there is contact between the first intermediate means and the solid dosage form on transfer of the powder material to the solid dosage form.

2. A method according to claim 1, wherein the powder material is applied to the first intermediate means by applying an electrostatic charge to the first intermediate means, and applying the powder material at a potential sufficiently different from the potential of the first intermediate means to cause the powder material to adhere to the first intermediate means.

3. A method according to claim 2, wherein the electrostatic charge is applied to the first intermediate means in a pattern.

4. A method according to claim 2, wherein the first intermediate means comprises a photo-conductive semiconductor at its surface.

5. A method according to claim 2, wherein the powder material has an electrostatic charge opposite to the electrostatic charge on the first intermediate means.

6. A method according to claim 5, wherein the electrostatic charge on the powder material is applied by triboelectric charging or corona charging.

7. A method according to claim 1, wherein the first intermediate means conforms to the shape of the solid dosage form on transfer of the powder material to the solid dosage form.

8. A method according to claim 1, wherein the powder material that adheres to the first intermediate means is transferred from the first intermediate means to the solid dosage form by means of the contact between the first intermediate means and the solid dosage form.

9. A method according to claim 1, wherein the powder material that adheres to the first intermediate means is transferred from the first intermediate means to the solid dosage form by electrostatic means.

10. A method of electrostatically applying a powder material to a solid dosage form, the method comprising the steps of electrostatically applying a powder material to a first intermediate means, and transferring the powder material that has been applied to the first intermediate means from the first intermediate means to the solid dosage form, wherein the powder material that has been applied to the first intermediate means is transferred from the first intermediate means to the solid dosage form via a second intermediate means.

11. A method according to claim 10, wherein there is contact between the first intermediate means and the second intermediate means on transfer of the powder material from the first intermediate means to the second intermediate means.

12. A method according to claim 10, wherein there is contact between the second intermediate means and the solid dosage form on transfer of the powder material from the second intermediate means to the solid dosage form.

13. A method according to claim 12, wherein the second intermediate means conforms to the shape of the solid dosage form on transfer of the powder material to the solid dosage form.

14. A method according to claim 1, wherein the method further comprises the step of treating the powder material to fix it on the solid dosage form once it has been transferred to the solid dosage form.

15. A method according to claim 1, wherein the method further comprises the step of treating the powder material to fix it on the solid dosage form as it is being transferred to the solid dosage form.

16. A method according to claim 14, wherein the treatment of the powder material to secure it to the solid dosage form results in the formation of a continuous coating on the solid dosage form.

17. A method according to claim 1, which comprises the step of applying powder material to a first surface of the solid dosage form, and the subsequent step of applying powder material to a second surface of the solid dosage form.

18. A method according to claim 1, wherein the method is carried out as a continuous process.

19. A method according to claim 1, wherein the powder material includes a biologically active material.

20. A method according to claim 1, wherein the solid dosage form is a pharmaceutical solid dosage form.

21. A method according to claim 20, wherein the solid dosage form is for human use.

22. A method according to claim 20, wherein the solid dosage form is a pharmaceutical tablet.

23. An apparatus for electrostatically applying a powder material to a solid dosage form, the apparatus comprising means for applying a powder material to a first intermediate means, and means for transferring the powder material that has been applied to the first intermediate means from the first intermediate means to the solid dosage form, wherein the first intermediate means is positioned such that there is contact between the first intermediate means and the solid dosage form on transfer of the powder material to the solid dosage form.

24. An apparatus according to claim 23, wherein the first intermediate means comprises a photo-conductive semiconductor.

25. An apparatus according to claim 23, wherein the first intermediate means is able to conform to the shape of the solid dosage form.

26. An apparatus for electrostatically applying a powder material to a solid dosage form, the apparatus comprising means for applying a powder material to a first intermediate means, and means for transferring the powder material that has been applied to the first intermediate means from the first intermediate means to the solid dosage form, wherein the apparatus further comprises means for transferring the powder material that has been applied to the first intermediate means to a second intermediate means, and means for transferring the powder material that has been transferred to the second intermediate means to the solid dosage form.

27. An apparatus according to claim 26, wherein the second intermediate means is positioned such that there is contact between the second intermediate means and the solid dosage form on transfer of the powder material to the solid dosage form.

28. An apparatus according to claim 27, wherein the second intermediate means is able to conform to the shape of the solid dosage form.

29. An apparatus according to claim 23, the apparatus further comprising means for treating the powder material to fix it on the solid dosage form once it has been transferred to the solid dosage form.

30. An apparatus according to claim 23, the apparatus further comprising means for treating the powder material to fix it on the solid dosage form as it is being transferred to the solid dosage form.

31. A coated substrate produced by a method according to claim 1.

32. An apparatus according to claim 26, wherein the first intermediate means comprises a photo-conductive semiconductor.

* * * * *